(12) United States Patent
Tian et al.

US011833489B2

(10) Patent No.: US 11,833,489 B2
(45) Date of Patent: Dec. 5, 2023

(54) CATALYST FOR PREPARING 2,3,3,3,-TETRAFLUOROPROPENE BY GAS-PHASE HYDRODECHLORINATION

(71) Applicant: XI'AN MODERN CHEMISTRY RESEARCH INSTITUTE, Shaanxi (CN)

(72) Inventors: Song Tian, Shaanxi (CN); Jian Lv, Shaanxi (CN); Wei Mao, Shaanxi (CN); Yanbo Bai, Shaanxi (CN); Zhaohua Jia, Shaanxi (CN); Bo Wang, Shaanxi (CN); Yue Qin, Shaanxi (CN); Hui Ma, Shaanxi (CN)

(73) Assignee: XI'AN MODERN CHEMISTRY RESEARCH INSTITUTE, Xi'an (CN)

( * ) Notice: Subject to any disclaimer, the term of this patent is extended or adjusted under 35 U.S.C. 154(b) by 73 days.

(21) Appl. No.: 17/609,771

(22) PCT Filed: Jun. 1, 2020

(86) PCT No.: PCT/CN2020/093696
§ 371 (c)(1),
(2) Date: Nov. 8, 2021

(87) PCT Pub. No.: WO2020/224663
PCT Pub. Date: Nov. 12, 2020

(65) Prior Publication Data
US 2022/0219146 A1    Jul. 14, 2022

(30) Foreign Application Priority Data
May 8, 2019   (CN) .......................... 201910380027.0

(51) Int. Cl.
| | | |
|---|---|---|
| *B01J 23/755* | (2006.01) | |
| *B01J 21/08* | (2006.01) | |
| *B01J 21/18* | (2006.01) | |
| *B01J 23/28* | (2006.01) | |
| *B01J 23/30* | (2006.01) | |
| *B01J 23/883* | (2006.01) | |
| *B01J 27/125* | (2006.01) | |
| *B01J 27/138* | (2006.01) | |
| *B01J 35/10* | (2006.01) | |
| *C07C 17/25* | (2006.01) | |

(52) U.S. Cl.
CPC ............ *B01J 23/755* (2013.01); *B01J 21/08* (2013.01); *B01J 21/18* (2013.01); *B01J 23/28* (2013.01); *B01J 23/30* (2013.01); *B01J 23/883* (2013.01); *B01J 27/125* (2013.01); *B01J 27/138* (2013.01); *B01J 35/1014* (2013.01); *B01J 35/1019* (2013.01); *B01J 35/1023* (2013.01); *B01J 35/1028* (2013.01); *C07C 17/25* (2013.01)

(58) Field of Classification Search
CPC . B01J 23/755; B01J 21/08; B01J 21/18; B01J 23/28; B01J 23/30; B01J 23/883; B01J 27/125; B01J 27/138; B01J 35/1014; B01J 35/1019; B01J 35/1023; B01J 35/1028; C07C 17/28
USPC ....... 502/184, 303–305, 324, 325, 337, 338, 502/345; 570/155, 135, 179
See application file for complete search history.

(56) References Cited

U.S. PATENT DOCUMENTS

| | | | |
|---|---|---|---|
| 8,058,486 B2 | 11/2011 | Merkel et al. | |
| 8,158,549 B2 * | 4/2012 | Wang .................. | B01J 27/13 502/224 |

FOREIGN PATENT DOCUMENTS

| | | | | |
|---|---|---|---|---|
| CN | 102603465 A | 7/2012 | | |
| CN | 102947254 A | 2/2013 | | |
| CN | 102947255 A | 2/2013 | | |
| CN | 103055843 A | 4/2013 | | |
| CN | 105251516 A | 1/2016 | | |
| CN | 105251518 A | 1/2016 | | |
| CN | 106179426 | * 12/2016 | ............ B01J 27/138 | |
| CN | 106179426 A | 12/2016 | | |
| CN | 108178719 A | 6/2018 | | |
| CN | 108367285 A | 8/2018 | | |
| WO | WO-2013055726 A1 * | 4/2013 | ............. B01J 19/02 | |

OTHER PUBLICATIONS

Translation of Written Opinion for PCT/CN2020/093696. (Year: 2020).*
Wei Mao et al., Highly Selective Dehydrochlorination of 1,1,1,2-Tetrafluoro-2-chloropropane to 2,3,3,3-Tetrafluoropropene over Alkali Metal Fluoride Modified MgO Catalysts, ChemCatChem, 2017, pp. 824-832, vol. 9.
Yusaku Takita et al., Decomposition of chlorofluorocarbons over metal phosphate catalysts Part I. Decomposition of CCl2F2 over metal phosphate catalysts, Phys. Chem. Chem. Phys., Jan. 1, 1999, pp. 2367-2372, vol. 1.
Yusaku Takita et al., Decomposition of chlorofluorocarbons over metal phosphate catalysis II. Origin of the stability of AlPO4 and the location of Ce as a promoter, Journal of Molecular Catalysis A: Chemical, 2000, pp. 111-119, vol. 155.

(Continued)

*Primary Examiner* — Patricia L. Hailey

(57) ABSTRACT

Disclosed is a catalyst for preparing 2,3,3,3-tetrafluoropropene by gas-phase hydrodechlorination, which solves the problem of the high costs and easy deactivation of traditional chlorofluorocarbon hydrodechlorination catalysts. The disclosed catalyst is characterized in consisting of an active component and a carrier, wherein the active component is a combination of one or more of the metals: Ni, Mo, W, Co, Cr, Cu, Ce, La, Mn and Fe. The catalyst in the present invention has excellent performance, high activity, good stability and a low reaction temperature, effectively reduces reaction energy consumption, and has industrial application value.

3 Claims, No Drawings

(56) References Cited

OTHER PUBLICATIONS

Yusaku Takita et al., Decomposition of chlorofluorocarbons over metal phosphate catalysts III. Reaction path of CCl2F2 decomposition over AlPO4, Applied Catalysis A: General, 2000, pp. 55-61, vol. 194-195.

International Search Report of PCT Patent Application No. PCT/CN2020/093696 dated Aug. 19, 2020.

* cited by examiner

CATALYST FOR PREPARING 2,3,3,3,-TETRAFLUOROPROPENE BY GAS-PHASE HYDRODECHLORINATION

TECHNICAL FIELD

The invention relates to a catalyst, in particular to a catalyst for preparing 2,3,3,3-tetrafluoropropene. It belongs to the heterogeneous catalysis technology field.

BACKGROUND 2,3,3,3-Tetrafluoropropene, referred to as HFO-1234yf, having a molecular formula of $CF_3CF=CH_2$, is non-toxic, non-flammable. Its ODP is zero, and GWP is about 4. It is considered as an ideal substitute for HFC-134a, and one of the most potential fourth-generation low-carbon refrigerants.

So far, among the prior synthesis methods of HFO-1234yf, 1,1,2,3-tetrachloropropene and anhydrous hydrogen fluoride are mainly used as raw materials to synthesize the target product (Chinese Patent CN102603465.A) through three steps. The last step is a dehydrochlorination reaction of 2-chloro-1,1,1,2-tetrafluoropropane (HCFC-244bb) in the presence of a catalyst. The step is usually carried out at a high temperature according to the Literature (Chem Cat Chem 2017, 9, 824) and patent U.S. Pat. No. 8,058,486B2, which not only consumes a lot energy but also easily causes carbon deposits to quickly deactivate the catalyst, and the industrial application value is low.

Chinese patents CN108178719.A, CN102947255.A, CN102947254.A have published 1,1-Dichloro-2,3,3,3-tetrafluoropropene or 1-chloro-2,3,3,3-tetrafluoropropene is used as the raw material compound to prepare HFO-1234yf through a process of hydrodechlorination, but the active components in the catalyst used for both the compounds are precious metal palladium, which are not easily available and expensive, leading to higher production costs.

It is reported a dechlorination reaction of $CCl_2F_2$ through decomposition on a $AlPO_4$ catalyst (Phys. Chem. Chem. Phys., 1999,1,2367; J. Mol. Catal. A: Chem. 2000,155,111 and Appl. Catal. A: Ge. 2000, 194, 55), and the reaction is performed at a temperature greater than 350° C.

At present, the process of preparing HFO-1234yf by selective hydrodechlorination has the problems that raw materials are not easily available and the catalyst is expensive. Based on this, in order to cope with the increasingly severe environmental protection situation and promote the industrial applications, there is an urgent need to design and prepare low-temperature, high-activity, environmentally friendly catalysts for HCFC-244bb gas phase selective hydrodechlorination to prepare HFO-1234yf.

SUMMARY OF THE INVENTION

The technical problem to be solved by the present invention is to provide a catalyst containing non-precious metal for selective gas-phase hydrodechlorination reaction for the preparation of HFO-1234yf, which is environment-friendly and active at a low temperature.

In order to achieve the object of the present invention, it is contemplated to prepare a catalyst through impregnation or co-precipitation of an active carrier and active component, wherein the active carrier is a solid material with a high specific surface area, and the active components is monometal or polymetal.

The catalyst for preparing 2,3,3,3-tetrafluoropropene by gas-phase hydrodechlorination of the present invention consists of an active component and a carrier, wherein the active component is one selected from the group consisting of metal Ni, Mo, W, Co, Cr, Cu, Ce, La, Mn, Fe, and any combination thereof. The carrier is one selected from the group consisting of an oxide, a fluoride activated carbon and a molecular sieve; wherein the active component accounts for 0.01%-50% of the total mass of the catalyst.

The carrier has a specific surface area of 10-2000 $m^2/g$.

The catalyst for preparing 2,3,3,3-tetrafluoropropene by gas-phase hydrodechlorination according to the present invention is used for preparing 2,3,3,3-tetrafluoropropene by a gas-phase selective hydrodechlorination reaction of 2-chloro-1,1,1,2-tetrafluoropropane. The reaction is carried out at a temperature of 100-300° C., under a reaction pressure 0.1~2.0 MPa. The feed gas space velocity is 20-200 $h^{-1}$; and the raw material hydrogen and 2-chloro-1,1,1,2-tetrafluoropropane are in a molar ratio of 1/1-5/1.

According to the invention, the method for preparing a catalyst for production of 2,3,3,3-tetrafluoropropene by gas-phase hydrodechlorination includes the following steps:

(1) Loading a metal salt aqueous solution on a carrier according to a loading amount by consecutive impregnation or co-impregnation to obtain a solid, aging the solid at room temperature for 8-12 h; then drying at a temperature of 90-120° C., calcinating a resulting product to obtain a catalyst precursor;

The metal salt is one selected from the group consisting of nickel nitrate, nickel chloride, nickel acetate, ammonium molybdate, ammonium tungstate, ammonium metatungstate, cobalt nitrate, cobalt chloride, cobalt hydroxide, chromium chloride, chromium nitrate, copper chloride, copper nitrate, cerium nitrate, lanthanum nitrate, manganese nitrate, manganese chloride, ferric nitrate, ferric chloride, ferrous nitrate, and ferrous chloride;

(3) Performing a temperature-programmed reduction to the catalyst precursor in a hydrogen atmosphere, and the reduction is carried out under a pressure of 0.2-1.2 MPa, at a $H_2$ flow rate of 80-120 mL/min and a temperature of 350-450° C. for 2-5 h, to finally obtain the catalyst.

Compared with the prior art, the present invention has the following beneficial technical effects:

① The present invention provides a catalyst that does not contain precious metal elements, has low raw material cost, is environmentally friendly, and has good resistance to high temperature sintering;

② It is reported in the prior literatures and patents that the high temperature conditions higher than 350° C. are required for the dehydrochlorination of HCFC-244bb. The catalyst provided by the present invention is applied to a selective hydrodechlorination reaction of HCFC-244bb, which can achieve a conversion rate of HCFC-244bb to 62% at 250° C. During the reaction, the selectivity of the target product HFO-1234yf reaches 63%. The catalyst can run stably for 200 h, having a long service life.

DETAILED DESCRIPTION OF ILLUSTRATED EXAMPLES

Specific embodiments of the present invention are given below, which will not limit the scope of the present invention. The performance evaluation of the catalyst used in the preparation of HFO-1234yf by hydrodechlorination according to the present invention is as follows:

Transfer 5 mL of the catalyst into a fixed-bed tubular reactor. After the catalyst bed temperature reaches 250° C., HCFC-244bb and hydrogen are introduced and contact with the catalyst bed for 4 s. The $H_2$ pressure is 0.2 MPa, and the $H_2$ and HCFC-244bb are in a mole ratio of 3. The product obtained after 8 hours of operation is subject to water washing and alkaline washing to remove hydrogen fluoride and hydrogen chloride, and then analyzed by gas chromatograph. The conversion rate of HCFC-244bb and the selectivity of the target product HFO-1234yf is calculated by the area normalization method.

Example 1

9.48 g (according to 20% Ni loading amount) nickel nitrate is added to deionized water to obtain a clear solution. 9.6 g of silica in an equal volume was immersed in the above solution, then aged at room temperature for 12 h, dried at 120° C. for 12 h to dry the moisture, and calcined at 500° C. for 4 h to obtain a $Ni/SiO_2$ oxide precursor. An in-situ temperature-programmed reduction is performed to prepare the catalyst. The temperature program mainly comprises two steps: (1) the precursor is heated from room temperature to a temperature of 120° C. at a heating rate of 5° C./min in a $H_2$ atmosphere (flow rate 150 mL/min). Then the temperature is kept at 120° C. for 1 h to eliminate moisture absorbed in the catalyst precursor. (2) the temperature is heated from 120° C. to 400° C. at a heating rate of 5° C./min, and kept for 2 h to obtain a catalyst. By taking the performance evaluation of the catalyst, the conversion rate of HCFC-244bb is 30.1%, and the HFO-1234yf selectivity is 50%.

Example 2

9.48 g (according to 20% Ni loading amount) nickel nitrate is added to deionized water to obtain a clear solution. 9.6 g of activated carbon in an equal volume was immersed in the above solution, then aged at room temperature for 12 h, dried at 120° C. for 12 h to dry the moisture, and calcined at 500° C. for 4 h to obtain a Ni/C oxide precursor. An in-situ temperature-programmed reduction is performed to prepare the catalyst. The temperature program mainly comprises two steps: (1) the precursor is heated from the room temperature to a temperature of 120° C. at a heating rate of 5° C./min in a $H_2$ atmosphere (flow rate 150 mL/min). Then the temperature is kept at 120° C. for 1 h to eliminate moisture absorbed in the catalyst precursor. (2) the temperature is heated from 120° C. to 400° C. at a heating rate of 5° C./min, and kept for 2 h to obtain a catalyst. By taking the performance evaluation of the catalyst, the conversion rate of HCFC-244bb is 48.9%, and the HFO-1234yf selectivity is 64%.

Example 3

9.48 g (according to 10% Ni loading amount) nickel nitrate is added to deionized water to obtain a clear solution. 21.9 g of magnesium fluoride in an equal volume was immersed in the above solution, then aged at room temperature for 12 h, dried at 120° C. for 12 h to dry the moisture, and calcined at 400° C. for 4 h to obtain a $Ni/MgF_2$ oxide precursor. An in-situ temperature-programmed reduction is performed to prepare the catalyst. The temperature program mainly comprises two steps: (1) the precursor is heated from the room temperature to a temperature of 120° C. at a heating rate of 5° C./min in a $H_2$ atmosphere (flow rate 150 mL/min). Then the temperature is kept at 120° C. for 1 h to eliminate moisture absorbed in the catalyst precursor. (2) the temperature is increased from 120° C. to 400° C. at a heating rate of 5° C./min, and kept for 2 h to obtain a catalyst. By taking the performance evaluation of the catalyst, the conversion rate of HCFC-244bb is 35.1%, and the selectivity of HFO-1234yf is 38%.

Example 4

9.48 g (according to a 10% Ni loading amount) nickel nitrate is added to deionized water to obtain a clear solution. 21.9 g of aluminum fluoride in an equal volume was immersed in the above solution, then aged at room temperature for 12 h, dried at 120° C. for 12 h to dry the moisture, and calcined at 500° C. for 4 h to obtain a $Ni/AlF_3$ oxide precursor. An in-situ temperature-programmed reduction is performed to prepare the catalyst. The temperature program mainly comprises two steps: (1) the precursor is heated from room temperature to a temperature of 120° C. at a heating rate of 5° C./min in a $H_2$ atmosphere (flow rate 150 mL/min). Then the temperature is kept at 120° C. for 1 h to eliminate moisture absorbed in the catalyst precursor. (2) the temperature is increased from 120° C. to 400° C. at a heating rate of 5° C./min, and kept for 2 h to obtain a catalyst. By taking the performance evaluation of the catalyst, the conversion rate of HCFC-244bb is 38.7%, and the selectivity of HFO-1234yf is 38%.

Example 5

3.52 g (according to a 20% Mo loading amount) ammonium molybdate is added to deionized water to obtain a clear solution. 7.65 g activated carbon in an equal volume was immersed in the above solution, then aged at room temperature for 12 h, dried at 120° C. for 12 h to dry the moisture, and calcined at 500° C. for 4 h to obtain a Mo/C oxide precursor. An in-situ temperature-programmed reduction is performed to prepare the catalyst. The heating program mainly comprises two steps: (1) the precursor is heated from room temperature to a temperature of 120° C. at a heating rate of 5° C./min in a $H_2$ atmosphere (flow rate 150 mL/min). Then the temperature is kept at 120° C. for 1 h to eliminate moisture absorbed in the catalyst precursor. (2) the temperature is increased from 120° C. to 400° C. at a heating rate of 5° C./min, and kept for 2 h to obtain a catalyst. By taking the performance evaluation of the catalyst, the conversion rate of HCFC-244bb is 45.7%, and the selectivity of HFO-1234yf is 51%.

Example 6

9.8 g (according to a 10% Ni loading amount) nickel nitrate and 4.6 g (according to a 10% Mo loading amount) ammonium molybdate are added to deionized water to obtain a clear solution. 20 g of activated carbon in an equal volume was immersed in the above solution, then aged at room temperature for 12 h, dried at 120° C. for 12 h to dry the moisture, and calcined at 500° C. for 4 h in a $N_2$ atmosphere to obtain a Ni—Mo/C oxide precursor. An in-situ temperature-programmed reduction is performed to prepare the catalyst. The temperature program mainly comprises two steps: (1) the temperature is heated from room temperature to a temperature of 120° C. at a heating rate of 5° C./min in a $H_2$ atmosphere (flow rate 150 mL/min). Then the temperature is kept at 120° C. for 1 h to eliminate moisture absorbed in the catalyst precursor. (2) the temperature is heated from 120° C. to 400° C. at a heating rate of 5° C./min, and kept for 2 h to obtain a catalyst. By taking the performance evaluation of the catalyst, the conversion rate of HCFC-244bb is 51.7%, and the HFO-1234yf selectivity is 59%.

Example 7

9.8 g (according to a 10% Ni loading amount) nickel nitrate and 9.5 g (according to a 20% Cu loading amount) copper nitrate are added to deionized water to obtain a clear solution. 20 g of activated carbon in an equal volume was immersed in the above solution, then aged at room temperature for 12 h, dried at 120° C. for 12 h to dry the moisture, and calcined at 500° C. for 4 h in a $N_2$ atmosphere to obtain a Ni—Cu/C oxide precursor. An in-situ temperature-programmed reduction is performed to prepare the catalyst. The temperature program mainly comprises two steps: (1) the temperature is heated from room temperature to a temperature of 120° C. at a heating rate of 5° C./min in a $H_2$ atmosphere (flow rate 150 mL/min). Then the temperature is kept at 120° C. for 1 h to eliminate moisture absorbed in the catalyst precursor. (2) the temperature is heated from 120° C. to 400° C. at a heating rate of 5° C./min, and kept for 2 h to obtain a catalyst. By taking the performance evaluation of the catalyst, the conversion rate of HCFC-244bb is 45.7%, and the HFO-1234yf selectivity is 70%.

Example 8

7.78 g (according to a 10% Ni loading amount) nickel nitrate, 3.68 g (according to a 10% Mo loading amount) ammonium molybdate and 3.80 g (according to a 5% Cu loading amount) copper nitrate are added to deionized water to obtain a clear solution. 15 g of activated carbon in an equal volume was immersed in the above solution, then aged at room temperature for 12 h, dried at 120° C. for 12 h to dry the moisture, and calcined at 500° C. for 4 h in a $N_2$ atmosphere to obtain a Ni—Mo—Cu/C oxide precursor. An in-situ temperature-programmed reduction is performed to prepare the catalyst. The temperature program mainly comprises two steps: (1) the temperature is heated from room temperature to a temperature of 120° C. at a heating rate of 5° C./min in a $H_2$ atmosphere (flow rate 150 mL/min). Then the temperature is kept at 120° C. for 1 h to eliminate moisture absorbed in the catalyst precursor. (2) the temperature is heated from 120° C. to 400° C. at a heating rate of 5° C./min, and kept for 2 h to obtain a catalyst. By taking the performance evaluation of the catalyst, the conversion rate of HCFC-244bb is 62%, and the HFO-1234yf selectivity is 63%.

Example 9

3.73 g (according to a 10% W loading amount) ammonium metatungstate is added to deionized water to obtain a clear solution. 10.4 g of activated carbon in an equal volume was immersed in the above solution, then aged at room temperature for 12 h, dried at 120° C. for 12 h to dry the moisture, and calcined at 500° C. for 4 h in a $N_2$ atmosphere to obtain a W/C oxide precursor. An in-situ temperature-programmed reduction is performed to prepare the catalyst. The temperature program mainly comprises two steps: (1) the temperature is heated from room temperature to a temperature of 120° C. at a heating rate of 5° C./min in a $H_2$ atmosphere (flow rate 150 mL/min). Then the temperature is kept at 120° C. for 1 h to eliminate moisture absorbed in the catalyst precursor. (2) the temperature is heated from 120° C. to 400° C. at a heating rate of 5° C./min, and kept for 2 h to obtain a catalyst. By taking the performance evaluation of the catalyst, the conversion rate of HCFC-244bb is 25.7%, and the HFO-1234yf selectivity is 36%.

Example 10

Service life test of the catalysts prepared for preparing of HFO-1234yf by hydrodechlorination of HCFC-244bb according to the present invention.

Performing a service life test to the catalyst prepared in the example 8. 5 mL of the catalyst is loaded to perform the hydrodechlorination reaction at 250° C. The hydrogen and HCFC-244bb are introduced in a molar ratio of 3 and contact with the catalyst bed for 4 s. The reaction continues for 200 h. The product obtained is subject to water washing and alkaline washing to remove hydrogen fluoride and hydrogen chloride, and then analyzed by gas chromatograph. The results of the test are indicted in Table 1.

TABLE 1

| Service life test | | |
| --- | --- | --- |
| Reaction time | HCFC-244bb conversion rate, % | HFO-1234yf selectivity, % |
| 24 h | 60.5 | 62.8 |
| 100 h | 60.8 | 63.4 |
| 150 h | 60.6 | 62.5 |
| 200 h | 60.4 | 61.8 |

The invention claimed is:

1. A catalyst for preparing 2,3,3,3-tetrafluoropropene by gas-phase hydrodechlorination, consisting of an active component and a carrier, wherein the active component is one selected from the group consisting of metal Ni, Mo, W, Co, Cr, Cu, Ce, La, Mn, Fe, and any combination thereof; the carrier is one selected from the group consisting of an oxide, activated carbon and a molecular sieve; wherein the active component accounts for 20%-50% of the total mass of the catalyst.

2. The catalyst for preparing 2,3,3,3-tetrafluoropropene by gas-phase hydrodechlorination according to claim 1, wherein the carrier has a specific surface area of 10-2000 $m^2/g$.

3. The catalyst for preparing 2,3,3,3-tetrafluoropropene by gas-phase hydrodechlorination according to claim 1, wherein the catalyst is used in a preparation of 2,3,3,3-tetrafluoropropene by a gas-phase selective hydrodechlorination reaction of 2-chloro-1,1,1,2-tetrafluoropropane carried out at a temperature of 100-300° C. and a reaction pressure of 0.1-2.0 MPa; a raw material gas space velocity is 20-200 $h^{-1}$; and the raw material hydrogen and 2-chloro-1,1,1,2-tetrafluoropropane are in a molar ratio of 1/1-5/1.

* * * * *